United States Patent [19]

Aoyagi

[11] Patent Number: 4,465,690

[45] Date of Patent: Aug. 14, 1984

[54] BROAD SPECTRUM FUNGICIDES

[75] Inventor: Edward I. Aoyagi, Petaluma, Calif.

[73] Assignee: Chevron Research Company, San Francisco, Calif.

[21] Appl. No.: 411,758

[22] Filed: Aug. 26, 1982

[51] Int. Cl.$^3$ .............. C07C 149/40; C07C 147/107; A01N 37/10

[52] U.S. Cl. .................. 424/308; 260/465 D; 560/11; 560/12; 560/15; 560/16; 424/304; 424/309

[58] Field of Search ............. 560/11, 12, 15, 16; 260/465 D; 424/304, 308, 309

[56] References Cited

U.S. PATENT DOCUMENTS

| | | | |
|---|---|---|---|
| 2,689,864 | 9/1954 | Emerson | 560/11 |
| 3,437,685 | 4/1969 | Brust | 560/11 |
| 3,637,803 | 1/1972 | Shen | 560/11 |
| 3,824,268 | 7/1974 | Mark | 560/15 |
| 3,988,375 | 10/1976 | Phillips | 560/15 |

Primary Examiner—Michael L. Shippen
Attorney, Agent, or Firm—S. R. LaPaglia; T. G. DeJonghe; S. L. Biggs

[57] ABSTRACT

Compounds of the formula:

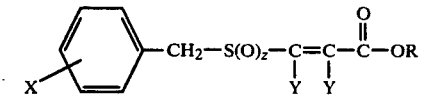

wherein X is hydrogen, halogen, lower alkyl, lower alkoxy, nitro, cyano, lower alkylthio, trihalomethyl or amino; Y is halogen; z is 0, 1 or 2; and R is lower alkyl, lower alkenyl or lower alkynyl, all optionally substituted with 1 to 3 halogen atoms, are fungicidal or intermediates in the preparation of fungicides.

33 Claims, No Drawings

BROAD SPECTRUM FUNGICIDES

BACKGROUND OF THE INVENTION

The present invention relates to certain aralkyl thio, sulfinyl or sulfonyl acrylates and their use as fungicides and algicides. In particular, I have found that the sulfinyl and sulfonyl derivatives of this invention show a particularly broad spectrum of fungicidal activity.

U.S. Pat. No. 3,437,685 discloses compounds of the formula:

$$RSO_2CH_2CX_2Y$$

wherein R represents benzyl or alkyl containing up to and including 12 carbon atoms, X represents halogen (which the specification limits to chlorine and bromine), and Y is a carboxylic acid derived group such as carboxyl, represented by the formula —COOH; nitrile, represented by the formula —CN; lower alkoxycarbonyl (carboxylic acid ester), represented by the formula —COOR$_1$; or carbamoyl represented by the formula —CONH$_2$, where R$_1$ represents alkyl containing up to and including four carbon atoms, which are useful as pesticides for the control of various insects, mites, fish bacteria, fungi, gastropods and plants.

U.S. Pat. No. 3,451,119 discloses a process for the preparation of alpha, beta unsaturated sulfones of the formula:

$$R-SO_2C=C-X$$
$$\phantom{R-SO_2}|\phantom{=}|$$
$$\phantom{R-SO_2}R_1\phantom{=}R_2$$

wherein R is alkyl having 1–18 carbon atoms, substituted alkyl having 1–18 carbon atoms, aryl, substituted aryl, cycloalkyl having up to 6 carbon atoms or a heterocyclic radical; R$_1$ and R$_2$ are hydrogen, alkyl, substituted alkyl, aryl, substituted aryl or acyl radical; and X is an electron withdrawing stablizing group such as: —CN, —COOR, —COOH, —COOM, —CONH$_2$, —COHNR, —CONRR, —SO$_2$R, —SO$_2$OR, —SO$_2$OR, —NO$_2$, —CHO AND —COR, where M is a cation. The sulfones produced thereby are disclosed as having "bioactive properties" which exhibit biological activity particularly in controlling microorganisms.

U.S. Pat. No. 4,021,482 discloses microbiologically active sulfinyl or sulfonyl 1-chloracrylic acid amides of the formula:

$$R_1S(O)_x-CH=CCl-\overset{O}{\underset{\|}{C}}-NHR_2$$

wherein R$_1$ represents C$_1$–C$_4$ alkyl; R$_2$ represents C$_1$–C$_8$ alkyl, or a cycloalkyl bound directly or by way of an alkylene bridge member, or a benzyl or phenyl radical which is unsubstituted or at most tri-substituted in the aromatic nucleus, and x represents the number 1 or 2. Alkyl radicals R$_1$ and R$_2$ are straight-chain or branched-chain hydrocarbon radicals, preferably ones having 1 to 4 carbon atoms, such as the methyl, ethyl, n-propyl, isopropyl, n-butyl, isobutyl, sec-butyl or tert-butyl radical. By cycloalkyl in the general formula is meant the following radicals: cyclopropyl, cyclobutyl, cyclopentyl and cyclohexyl. The alkylene bridge for cycloalkyl radicals is preferably the methylene group. Benzyl as well as phenyl can be up to tri-substituted or they can be unsubstituted. Substituents can be: methyl, ethyl, halogen, nitro, haloalkyl—preferably trifluoromethyl—or C$_1$–C$_3$ alkoxy.

U.S. Pat. No. 3,159,666 discloses arylsulfonyl alkenenitriles of the formula:

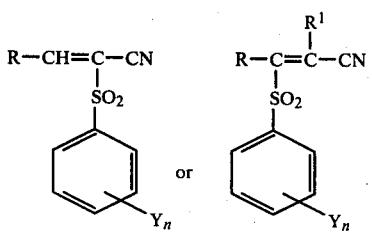

wherein R and R' are selected from the class consisting of hydrogen or a hydrocarbon radical free of aliphatic unsaturation and containing from 1 to 6 carbon atoms, and R and R' can be the same or different, Y is selected from the class consisting of chlorine, bromine, iodine, fluorine, hydrogen and alkyl radicals having from 1 to 6 carbon atoms, and n represents an integer from 1 to 5, which inhibit the growth of microorganisms such as bacteria and fungi.

SUMMARY OF THE INVENTION

The aralkyl thio, sulfinyl or sulfonyl acrylate compounds of this invention are represented by the formula:

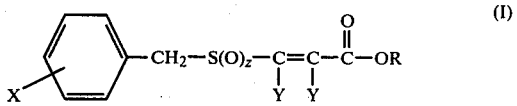

(I)

wherein X is hydrogen, halogen, lower alkyl, lower alkoxy, nitro, cyano, lower alkylthio, trihalomethyl or amino; Y is halogen; z is 0, 1 or 2; and R is lower alkyl, lower alkenyl, or lower alkynyl, all optionally substituted with 1 to 3 halogen atoms.

Among other factors, the present invention is based on my finding that the sulfinyl and sulfonyl compounds of this invention are surprisingly effective in controlling a very broad spectrum of fungi. In particular, sulfinyl compounds exhibit an especially broad range of fungicidal activity. In addition, some of the sulfinyl and sulfonyl compounds exhibit algicidal activity.

The corresponding sulfide compounds are useful as intermediates in the preparation of the sulfoxides and sulfones. In addition, some of the sulfides exhibit fungicidal activity.

Preferred are compounds where R is lower alkyl. Also preferred are compounds where X is hydrogen or halogen and z is 1 or 2. Especially preferred are compounds where z is 1.

As is apparent the compounds may have assymetric carbon atoms and, thus, can exist as optical isomers. Accordingly, the respective optical isomers and geometric isomers, as well as mixtures thereof, are encompassed with the invention. Representative compounds of this invention are included in Table I.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, butyl, and the like.

The term "alkenyl" refers to unsaturated alkyl groups having a double bond [e.g., $CH_3CH=CH-(CH_2)_2-$] and includes both straight- and branched-chain alkenyl groups. "Lower alkenyl" refers to groups having a total of from 3 to 6 carbon atoms. Typical lower alkenyl groups include, for example, propenyl, but-3-enyl, pent-4-enyl, and the like.

The term "halo" or "halogen" refers to the groups fluoro, chloro, bromo and iodo.

The term "alkynyl" refers to unsaturated alkyl groups having a triple bond (e.g., $CH_1\equiv C-CH_2CH_2-$) and includes both straight- and branched-chain alkynyl groups. "Lower alkynyl" refers to groups having a total of from 2 to 6 carbon atoms. Typical lower alkynyl groups include propynyl, butynyl, and the like.

The term "alkoxy" refers to group R'O— wherein R' is alkyl. The term "lower alkoxy" refers to alkoxy groups having from 1 to 6 carbon atoms; examples include methoxy, ethoxy, isopropoxy, and the like.

The term "alkylthio" refers to the group R'S— wherein R' is alkyl. The term "lower alkylthio" refers to alkylthio groups having 1 to 6 carbon atoms; examples include methylthio, ethylthio, isopropylthio, and the like.

The term "alkylene" refers to the group $-(CH_2)_x-$ wherein x is an integer one or greater and includes, for example, methylene, ethylene, propylene and the like.

The term "aryl" refers to aryl groups having from 6 to 10 carbon atoms which may be substituted with one or more substituents and includes, for example, phenyl, p-chlorophenyl, m-methyl-phenyl, o-ethylphenyl and the like.

The term "aralkyl" refers to an alkyl group of 1 to 4 carbon atoms substituted with an aryl group of from 6 to 10 carbon atoms and includes, for example, p-chlorobenzyl, p-methylbenzyl, m-methylbenzyl, 2-phenylethyl, o-ethylbenzyl and the like.

The term "sulfide" or thio refers to the group or a compound having the group $-S(O)_z-$ where z is 0, that is —S—.

The term "sulfinyl" or "sulfoxide" refers to the group or a compound having the group $-S(O)_z-$ where Z is 1, that is —SO—.

The term "sulfonyl" or "sulfone" refers to the group or a compound having the group $-S(O)_z$ where z is 2, that is

DETAILED DESCRIPTION OF THE INVENTION

The compounds of this invention may be prepared according to the following reaction sequences:

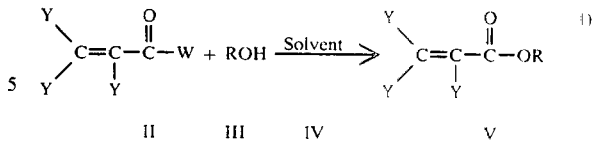

wherein W is chloro and Y and R are as previously defined in conjunction with Formula I.

Reaction (1) is carried out by mixing II and III in IV and stirring from about 1 to about 72 hours. For convenience, the reaction is carried out at ambient temperature and pressure. Suitable solvents include inert organic solvents such as methylene chloride, toluene, chloroform, ethyl acetate and the like. Although roughly equimolar amounts of II and III may be used, it is preferably to use a slight excess of III. The product V may be isolated by conventional procedures or alternatively used as a crude prep after removing the solvent.

The sulfide compounds of formula I, where z is 0 are prepared by reacting V with a aralkyl thiol according to the following reaction sequence:

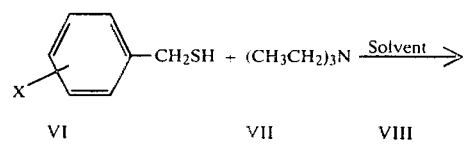

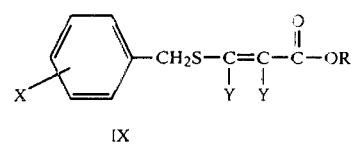

wherein Y, X, Y and R are as defined previously in conjunction with formula I and reaction (1).

Reaction (2) is carried out by stirring V, VI and VII in VIII for about 1 to about 72 hours. For convenience, the reaction may be carried out at ambient temperature and pressure. Suitable solvents include dimethoxyethane, methylene chloride, toluene and the like. The product IX is isolated by conventional procedures such as stripping, extraction, filtration, chromatography and the like.

The sulfoxide or sulfone compounds of formula I, that is, where z is 1 or 2, corresponding to products IX, may be prepared from the corresponding sulfide by selective oxidation of the thio group according to the following reaction:

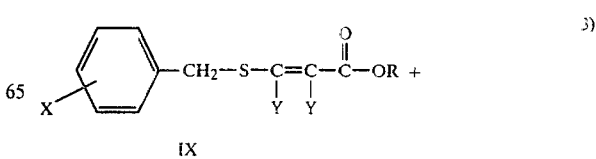

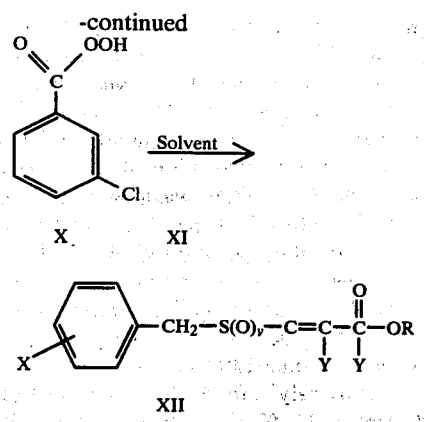

-continued

XII: (X)-⟨ring⟩-CH$_2$-S(O)$_v$-C=C-C(=O)-OR with Y, Y substituents wherein X, Y and R are as defined in conjunction with formula I and v is 1 or 2.

Reaction (3) is conducted by adding X to a stirred solution of IX in XI. The reaction mixture is stirred at ambient temperature for about 2 to about 72 hours. The product XII is then isolated by conventional procedures such as extraction, filtration, stripping, chromatography and the like. Although chloroform is the preferred solvent XI, other suitable solvents include other chlorinated hydrocarbon solvents such as methylene chloride and other inert organic solvents. It is well established that peroxides such as meta-chloro-perbenzoic acid (MCPBA) (X) and the like oxidize thio derivatives (such as IX) to the corresponding sulfoxide or sulfone. To obtain the sulfoxide, $v=1$, corresponding to IX, X is added in the ratio of approximately one equivalent X per equivalent IX. Addition of X in the ratio of about two or more equivalents X per equivalent XI yields the corresponding sulfone ($v=2$). In some cases, the oxidation reaction may yield mixtures of sulfoxide and sulfone; however, the individual components may be separated using conventional techniques such as chromatography.

The sulfoxide and sulfone compounds of this invention are useful for controlling fungi, particularly plant fungal infections and late blights, including those listed in Table II. However, some fungicidal compounds of this invention may be more fungicidally active than others against particular fungi. The sulfide compounds of this invention are used in intermediates in the synthesis of the corresponding sulfoxides and sulfones. In addition, some of the sulfide compounds of this invention exhibit fungicidal activity. However, in general, the sulfoxide and sulfone compounds exhibit a greater fungicidal activity and a wider range of fungicidal activities than the analogous sulfides. Also, the sulfoxide compounds generally exhibit broader a spectrum of activity and greater fungicidal activity than the corresponding sulfone compounds.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carriers, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

Many of the compounds of the invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, streams, canals, pools, and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep, 0.1 to 10 ppm is equal to about 0.3 to 30 pounds per acre of water one foot deep. These compounds may be applied to the aqueous growth environments of such organisms as dispersible powders or in solution with water-miscible solvents.

In addition, some of the compounds of the present invention exhibit herbicidal activity, generally in post-emergent applications. For post-emergent applications, the herbicidal compounds will be applied directly to the foliage and other plant parts. Generally, those compounds exhibiting herbicidal activity are effective against weed grasses as well as broad-leaved weeds. Some compounds may be selective with respect to the type of application and/or type of weed.

A further understanding of my invention may be had from the following non-limiting examples.

EXAMPLES

Example 1

Preparation of

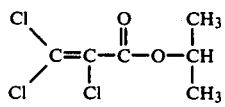

Isopropyl Trichloroacrylate

A solution of 6.5 gms (0.108 moles) isopropyl alcohol, 20 gms (0.013 moles) trichloro acryloyl chloride and 100 ml methylene chloride was stirred for 72 hours. The solvent was stripped and the product was used in subsequent reactions without further purification.

Example 2

Preparation of

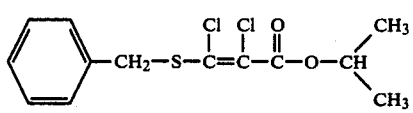

To a stirred mixture of 4.6 gms (0.037 moles) of benzoyl mercaptan and 3.8 gms (0.037 moles) triethylamine in dimethoxyethane, 8.0 gms (0.037 moles) of the product of Example 1 in dimethoxyethane was added in a dropwise manner. The total volume of dimethoxyethane used was 50 ml. The addition caused a slight exothermia and a white precipitate formed immediately. The mixture was allowed to stir overnight at room temperature. The mixture was filtered and the solvent stripped to give the crude product as an oil. The oil was chromatographed on silica gel, eluting first with hexane, and then with hexane and increasing amounts of methylene chloride. The product was eluted with 10% methylene chloride in hexane. The product was a mixture of cis and trans isomers (as determined by NMR).

Elemental analysis for $C_{13}H_{14}Cl_2O_2S$ showed: calculated % C 51.15, % H 4.63, and % N O; found % C 53.85, % H 5.14, and % N 0.24.

EXAMPLE 3

Preparation of

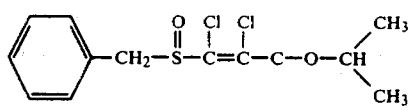

and

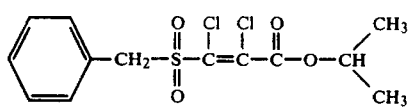

To a stirred mixture of 4.0 gms (0.0131 moles) of the product of Example 2 in 100 ml chloroform, 5 gms (0.29 moles) of meta-chloropenbenzoic acid was added. The reaction mixture was allowed to stir at ambient temperature for 2 days. Thin layer chromatography showed two major products.

The reaction mixture was washed twice with a saturated aqueous sodium bicarbonate solution. The solvent was stripped to give an oil which was chromatographed on silica gel.

Eluting with methylene chloride gave the sulfone. Stripping of the solvent followed by hardtopping gave 2.5 gms of the sulfone (a cis-trans mixture) a light yellow cloudy oil. Elemental analysis for $C_{13}H_{14}Cl_2O_4S$ showed: calculated % C 46.30, % H 4.18, and % N 0.0; found % C 47.23, % H 4.75, and % N 0.07.

Eluting with 10% ethyl acetate in methylene chloride gave the sulfoxide. Stripping of the solvent yielded 1.2 gms of the sulfoxide, a light yellow oil which solidified upon standing. Elemental analysis for $C_{13}H_{14}Cl_2O_3S$ showed: calculated % C 48.60, % H 4.18; and % N 0.0; found % C 51.16, % H 4.83, and % N 0.14.

Example 4

Preparation of

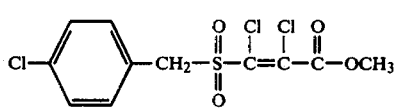

To a stirred mixture of 4.2 gms (0.0135 moles)

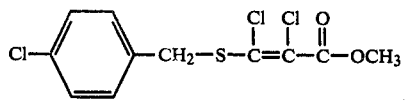

in 100 ml chloroform, 5.2 gms (0.030 moles) meta-chloroperoxybenzoic acid were added carefully. The resulting mixture was stirred two days at room temperature. The reaction mixture was washed twice with a saturated aqueous sodium bicarbonate solution and then dried over magnesium sulfate. Stripping of the solvent gave the product, a light yellow oil. The structure was confirmed by the NMR and IR spectra. The oil crystallized overnight to give a light yellow solid.

Elemental analysis showed: calculated % C 38.44, % H 2.64, and % N 0.0; found % C 39.53, % H 2.8, and % N 0.04.

Compounds made in a manner consistent with Examples 1 to 4 are found in Table I.

Example 5

Mycelial Inhibition

A number of the compounds of the present invention were evaluated for in vitro fungicidal effectiveness by means of a mycelial inhibition test. This test is designed to measure the fungitoxic activity of fungicidal chemicals in terms of their degree of inhibition of mycelium growth. Fungi used were *Phythium ultimum, Rhizoctonia solani, Fusarium monilofroma, Botrytis cinerea* and *Aspargillos niger.* Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip in terms of mg/cm$^2$ needed for 99% control of the fungus (ED$_{99}$). The effectiveness of the compounds tested for fungicidal activity is reported in Table II in terms of the percent of the ED$_{99}$ of the test compound of the ED$_{99}$ of the standard Difolatan ®.

Example 6

Grape Downy Mildew Control

The compounds of the invention were tested for the control of the Grape Downy Mildew organism *Plasmopara viticola*. Detached leaves, between 70 and 85 mm in diameter, of 7-week-old *Vitis vinifera* grape seedlings (cultivar Emperor) were used as hosts. The leaves were sprayed with a solution of the test compound in acetone. The sprayed leaves were dried, inoculated with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

Example 7

Tomato Late Blight

Compounds of this invention were tested for the preventive control of the Tomato Late Blight organism *Phytophthora infestans*. Five- to six-week-old tomato seedlings (cultivator Bonny Best) were used. The tomato plants were sprayed with a 250 ppm suspension of the test compound in acetone, water and a small amount of a nonionic emulsifier. The sprayed plants were then inoculated 1 day later with the organism placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

Example 8

Celery Late Blight

The Celery Late Blight tests were conducted using celery plants (Utah) 11 weeks old. The Celery Late Blight organism was *Septoria apii*. The celery plants were sprayed with solutions of the candidate toxicant (test compound) mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant (test compound) is based on the percent disease reduction relative to untreated check plants. The results are reported in Table II.

Example 9

Tomato Early Blight

Compounds of this invention were tested for the control of the Tomato Early Blight organism *Alternaria solani conida*. Tomato seedlings (variety Bonny Best) of 6 to 7 weeks old were used. The tomato plants were sprayed with a 250 ppm solution of the test compound in an acetone-and-water solution containing a small amount of nonionic emulsifier. The sprayed plants were inoculated 1 day layer with the organism, placed in an environmental chamber and incubated at 66° F. to 68° F. and 100% relative humidity for 24 hours. Following the incubation, the plants were maintained in a greenhouse for about 12 days. Percent disease control provided by a given test compound was based on a comparison to the percent disease development on untreated check plants. The compounds tested and the results are tabulated in Table II.

Example 10

Bean Rust Eradication

Compounds of this invention were tested for the eradication of Bean Rust, using 16 to 19 day old pinto bean plants. The pinto bean plants were inoculated with *Uromyces phaseoli typica* in an environmental chamber set for 100% relative humidity and 20°–21° C. After the Bean Rust has developed, one half of the plants are sprayed with solutions of the test compound in acetone. The percent disease control is determined based on the percent disease control reduction in the plants treated with test solution relative to the untreated plants. The results are tabulated in Table II.

Example 11
Bean Powdery Mildew

The compounds of the invention were tested for control of the Bean Powdery Mildew organism *Erisiphe polygoni*. Seedling bean plants were sprayed with a 250 ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to untreated check plants. The results are tabulated in Table II.

Example 12
Rise Blast

Compounds of this invention were tested for control of the Rice Blast organisms, *Piricularia oryzae*, using 10 to 14 day old rice plant seedlings (Calrose M-9 variety). Seedling plants were sprayed with a 625 ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on untreated check plants:

$$\% \text{ Control} = 100 \times \frac{\% \text{ disease in treated plants}}{\% \text{ disease in check}}$$

The results are tabulated in Table II.

Example 13
Algae and Aquatic Weeds Control

Representative compounds of the invention were tested as aquatic herbicides and algicides by the following method. The weed test species were *Lemna minor* and *Elodea canadensis* and the algae used was *Spirulina maxima*.

An acetone solution of the test compound and a small amount of an alkylarylpolyoxyethylene glycol-containing surfactant was prepared. This solution was mixed with a nutrient solution in quantity sufficient to give a concentration of 2 ppm. Eight oz. plastic cups were filled with 150 ml of this solution. A sample of the test, Lemna and Elodea, was added together to each cup. Forty ml of Spirulina culture with the 2 ppm treatment was placed in 1½ oz. plastic cups or #4 glass vials. The containers were then placed in an illuminated environment and maintained at a temperature of about 20° C. for incubation. The containers were observed periodically for growth (as compared with an untreated check). The effectiveness of the test compound was determined based on a final observation of growth after 7 to 10 days. The results of the test on a 0-to-100 basis—0 indicating no effectiveness and 100 indicating complete effectiveness—are reported in Table III.

TABLE I

Compounds of the formula

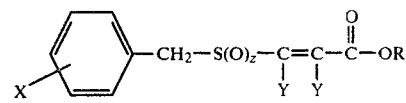

| Compound | | | | | Physical | 100% | | % H | | % N | |
|---|---|---|---|---|---|---|---|---|---|---|---|
| No. | X | Y | z | R | State | Calc. | Found | Calc. | Found | Calc. | Found |
| 1 38164 | 4-Cl | Cl | 2 | CH$_3$ | light yellow solid | 38.44 | 39.53 | 2.64 | 2.8 | 0 | 0.04 |
| 2 38741 | H | Cl | 0 | CH$_3$ | clear oil | 47.66 | 50.4 | 3.64 | 4.54 | 0 | 0.16 |
| 3 38743 | H | Cl | 1 | CH$_3$ | light yellow viscous oil | 45.06 | 46.31 | 3.44 | 3.62 | 0 | 0.11 |
| 4 38742 | H | Cl | 2 | CH$_3$ | light yellow viscous oil | 42.73 | 44.51 | 3.26 | 3.41 | 0 | 0.01 |
| 5 38654 | H | Cl | 0 | CH(CH$_3$)$_2$ | colorless oil | 51.15 | 53.85 | 4.63 | 5.14 | 0 | 0.24 |
| 6 38702 | H | Cl | 1 | CH(CH$_3$)$_2$ | lt. yellow solid, mp 34–42° C. | 48.6 | 51.16 | 4.39 | 4.83 | 0 | 0.14 |
| 7 38656 | H | Cl | 2 | CH(CH$_3$)$_2$ | light yellow oil | 46.30 | 47.23 | 4.18 | 4.75 | 0 | 0.07 |
| 8 38655 | 4-Cl | Cl | 0 | CH(CH$_3$)$_2$ | colorless oil | 45.96 | 47.24 | 3.86 | 4.29 | 0 | 0.04 |
| 9 38703 | 4-Cl | Cl | 1 | CH(CH$_3$)$_2$ | yellow solid, mp 67–72° C. | 43.9 | 45.99 | 3.69 | 4.3 | 0 | 0.11 |
| 10 38843 | 4-Cl | Cl | 2 | CH(CH$_3$)$_2$ | white solid, mp 107–115° C. | 42.01 | 42.77 | 3.53 | 4.17 | 0 | 0.03 |

TABLE II

| Compound No. | Pythium | Rhizoc. | Fusarium | Botrytis | Aspen | Grape Downy Mildew | Tomato Late Blight | Celery Late Blight | Tomato Early Blight | Bean Rust Erad. | Bean Powdery Mildew | Rice Blast |
|---|---|---|---|---|---|---|---|---|---|---|---|---|
| 1 38164 | 19 | 33 | 32 | 22 | 71 | 100 | 92 | 95 | 69 | 0 | 7 | 91 |
| 2 38741 | 0 | 0 | 0 | 0 | 0 | 0 | 7 | 13 | 0 | 0 | 0 | 0 |
| 3 38743 | 53 | 100 | 49 | 43 | 96 | 100 | 77 | 75 | 0 | 4 | 0 | 100 |
| 4 38742 | 36 | 100 | 44 | 39 | 53 | 100 | 27 | 85 | 0 | 0 | 0 | 100 |
| 5 38654 | 0 | 0 | 0 | 0 | 0 | 18 | 0 | 0 | 0 | 0 | 0 | 0 |
| 6 38702 | 25 | 36 | 38 | 37 | 64 | 100 | 90 | 88 | 50 | 0 | 33 | 96 |
| 7 38656 | 0 | 0 | 0 | 0 | 0 | 100 | 87 | 73 | 23 | 0 | 42 | 98 |
| 8 38655 | 0 | 0 | 0 | 0 | 0 | 73 | 0 | 13 | 0 | 0 | 0 | 0 |
| 9 38703 | 31 | 62 | 38 | 28 | 67 | 100 | 53 | 81 | 50 | 4 | 89 | 100 |
| 10 38843 | 0 | 0 | 0 | 0 | 143 | 100 | 33 | 33 | 42 | 0 | 0 | — |

TABLE III

| Compound No. | Algicidal Activity | | |
|---|---|---|---|
| | Spirulina | Memna | Elodea |
| 1 38164 | 90 | 0 | 80 |
| 2 38741 | — | 0 | 0 |
| 3 38743 | — | 55 | 80 |
| 4 38742 | — | 55 | 95 |
| 5 38654 | 0 | 0 | 0 |
| 6 38702 | 70 | 15 | 83 |
| 7 38656 | 0 | 0 | 70 |
| 8 38655 | 0 | 0 | 0 |
| 9 38703 | 70 | 20 | 93 |
| 10 38843 | 70 | 0 | 0 |

What is claimed is:

1. A compound of the formula:

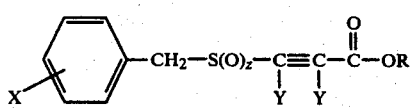

wherein X is hydrogen, halogen, lower alkyl, lower alkoxy, nitro, cyano, lower alkylthio, trihalomethyl or amino; Y is halogen; z is 0, 1 or 2; or R is lower alkyl, lower alkenyl or lower alkynyl, optionally substituted with 1 to 3 halogen atoms.

2. A compound according to claim 1 wherein R is lower alkyl.

3. A compound according to claim 2 wherein X is hydrogen or halogen.

4. A compound according to claim 3 wherein Y is chloro.

5. A compound according to claim 4 wherein z is 1 or 2.

6. A compound according to claim 5 wherein X is hydrogen or 4-chloro.

7. A compound according to claim 6 wherein X is 4-chloro, z is 2 and R is methyl.

8. A compound according to claim 6 wherein R is isopropyl.

9. A compound according to claim 8 wherein z is 1.

10. The compound according to claim 9 wherein X is 4-chloro.

11. The compound according to claim 9 wherein X is hydrogen.

12. A composition for controlling fungi comprising a biologically inert carrier and a fungicidally effective amount of a compound of claim 1.

13. A composition for controlling fungi comprising a biologically inert carrier and a fungicidally effective amount of a compound of claim 2.

14. A composition for controlling fungi comprising a biologically inert carrier and a fungicidally effective amount of a compound of claim 3.

15. A composition for controlling fungi comprising a biologically inert carrier and a fungicidally effective amount of a compound of claim 4.

16. A composition for controlling fungi comprising a biologically inert carrier and a fungicidally effective amount of a compound of claim 5.

17. A composition for controlling fungi comprising a biologically inert carrier and a fungicidally effective amount of a compound of claim 6.

18. A composition for controlling insects comprising a biologically inert carrier and a fungicidally effective amount of a compound of claim 7.

19. A composition for controlling insects comprising a biologically inert carrier and a fungicidally effective amount of a compound of claim 8.

20. A composition for controlling insects comprising a biologically inert carrier and a fungicidally effective amount of a compound of claim 9.

21. A composition for controlling insects comprising a biologically inert carrier and a fungicidally effective amount of a compound of claim 10.

22. A composition for controlling insects comprising a biologically inert carrier and a fungicidally effective amount of a compound of claim 11.

23. A method of controlling fungi which comprises contacting said fungi or their growth environment with a fungicidally effective amount of a compound of the formula:

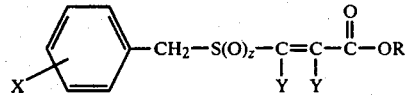

wherein X is hydrogen, halogen, lower alkyl, lower alkoxy, nitro, cyano, lower alkylthio, trihalomethyl or amino; Y is halogen; z is 0, 1 or 2; and R is lower alkyl, lower alkenyl or lower alkynyl, optionally substituted with 1 to 3 halogen atoms.

24. The method of claim 23 wherein R is lower alkyl.

25. The method of claim 24 wherein X is hydrogen or halogen.

26. The method of claim 25 wherein Y is chloro.

27. The method of claim 26 wherein z is 1 or 2.

28. The method of claim 27 wherein X is hydrogen or 4-chloro.

29. The method of claim 28 wherein X is 4-chloro, z is 2 and R is methyl.

30. The method of claim 28 wherein R is isopropyl.

31. The method of claim 30 wherein z is 1.

32. The method of claim 31 wherein X is 4-chloro.

33. The method of claim 31 wherein X is hydrogen.

* * * * *